United States Patent [19]
Hood, Jr. et al.

[11] Patent Number: 5,680,870
[45] Date of Patent: Oct. 28, 1997

[54] OSCILLOMETRIC BLOOD PRESSURE MONITOR WHICH ACQUIRES BLOOD PRESSURE SIGNALS FROM COMPOSITE ARTERIAL PULSE SIGNAL

[75] Inventors: Rush W. Hood, Jr., Tampa; Charles A. Wells, Clearwater; Richard Medero, Tampa, all of Fla.

[73] Assignee: Johnson & Johnson Medical, Inc., New Brunswick, N.J.

[21] Appl. No.: 368,418

[22] Filed: Jan. 4, 1995

[51] Int. Cl.$^6$ ............................................. A61B 5/02
[52] U.S. Cl. .................................................. 128/682
[58] Field of Search ............................ 128/672, 677, 128/680-3

[56] References Cited

U.S. PATENT DOCUMENTS

| | | | |
|---|---|---|---|
| 4,349,034 | 9/1982 | Ramsey, III | 128/681 |
| 4,360,029 | 11/1982 | Ramsey, III | 128/681 |
| 4,461,266 | 7/1984 | Hood, Jr. et al. | 128/681 |
| 4,543,962 | 10/1985 | Medero et al. | 128/682 |
| 4,546,775 | 10/1985 | Medero | 128/681 |
| 4,627,440 | 12/1986 | Ramsey, III et al. | 128/682 |
| 4,638,810 | 1/1987 | Ramsey, III et al. | 128/681 |
| 4,754,761 | 7/1988 | Ramsey, III et al. | 128/683 |
| 4,774,960 | 10/1988 | Arnold et al. | 128/681 |
| 4,889,133 | 12/1989 | Nelson et al. | 128/681 |
| 4,926,873 | 5/1990 | Frankenreiter | 128/681 |
| 4,949,710 | 8/1990 | Dorsett et al. | 128/680 |
| 4,984,577 | 1/1991 | Frankenreiter | 128/681 |
| 5,052,397 | 10/1991 | Ramsey, III et al. | 28/682 |
| 5,054,495 | 10/1991 | Uemura et al. | 128/680 |
| 5,103,833 | 4/1992 | Apple | 128/687 |
| 5,115,189 | 5/1992 | Holcomb | 324/121 |
| 5,134,399 | 7/1992 | Hiller | 341/131 |
| 5,170,795 | 12/1992 | Ramsey, III et al. | 128/682 |
| 5,218,968 | 6/1993 | Apple | 128/687 |
| 5,253,648 | 10/1993 | Walloch | 128/681 |
| 5,261,413 | 11/1993 | Kawahara | 128/682 |
| 5,279,303 | 1/1994 | Kawamura et al. | 128/683 |
| 5,280,790 | 1/1994 | Brooks | 128/681 |
| 5,311,872 | 5/1994 | Apple | 128/687 |

*Primary Examiner*—John P. Lacyk
*Attorney, Agent, or Firm*—Woodcock Washburn Kurtz Mackiewicz & Norris LLP

[57] ABSTRACT

An automated sphygmo-manometer which digitizes the pressure transducer output with sufficient resolution to preserve the details of the measured oscillation complexes. The "composite" arterial pulse signal containing the DC pressure component and the oscillation complexes is processed in a single processing channel so that the amplitudes of the oscillation pulse can be measured in the presence of the static components. Any necessary filtering is performed in the digital domain using known digital signal processing (DSP) techniques. In addition, dither signals may be added to the arterial pulse signal in the single processing channel in order to increase the apparent resolution. A simple finite impulse response (FIR) filter is used to sum respective samples to form high resolution samples from a plurality of low resolution samples. The FIR filter has zero crossings at the summing frequencies for the dither signal so as to eliminate the dither signal from the high resolution sum signal prior to determining the blood pressure from the composite signal using pulse separation and blood pressure calculation software.

4 Claims, 6 Drawing Sheets

OSCILLOMETRIC BLOOD PRESSURE MONITOR WHICH ACQUIRES BLOOD PRESSURE SIGNALS FROM COMPOSITE ARTERIAL PULSE SIGNAL

FIELD OF THE INVENTION

This invention relates to automated blood pressure monitoring, and more particularly, to automated blood pressure monitors that utilize a pneumatic cuff for accomplishing a sphygmomanometric measurement on a patient.

BACKGROUND OF THE INVENTION

The sphygmomanometric class of automated blood pressure monitors employs an inflatable cuff to exert controlled counter-pressure on the vasculature of a patient. One large class of such monitors, exemplified by that described in U.S. Pat. Nos. 4,349,034 and 4,360,029, both to Maynard Ramsey, III and commonly assigned herewith and incorporated by reference, employs the oscillometric methodology. In accordance with the Ramsey patents, an inflatable cuff is suitably located on the limb of a patient and is pumped up to a predetermined pressure above the systolic pressure. Then, the cuff pressure is reduced in predetermined decrements, and at each level, pressure fluctuations are monitored. The resultant arterial pulse signals typically consist of a DC voltage with a small superimposed variational component caused by arterial blood pressure pulsations (referred to herein as "oscillation complexes" or just simply "oscillations"). The oscillation complexes typically have amplitudes which are typically about one percent that of the arterial pulse signals. After suitable filtering to reject the DC component (arterial pulse signal) and to provide amplification by a scale factor, peak pulse amplitudes (PPA) above a given base-line are measured and stored. As the decrementing continues, the peak amplitudes will normally increase from a lower level to a relative maximum, and thereafter will decrease. These amplitudes form an oscillometric envelope for the patient. The lowest cuff pressure at which the oscillations have a maximum value has been found to be representative of the mean arterial pressure ("MAP"). Systolic and diastolic pressures can be derived either as predetermined fractions of MAP, or by more sophisticated methods of direct processing of the oscillation complexes.

The step deflation technique as set forth in the Ramsey patents is the commercial standard of operation. A large percentage of clinically acceptable automated blood pressure monitors utilize the step deflation rationale. When in use, the blood pressure cuff is placed on the patient and the operator typically sets a time interval, typically from 1 to 90 minutes, at which blood pressure measurements are to be made. The noninvasive blood pressure ("NIBP") monitor automatically starts a blood pressure determination at the end of the set time interval.

FIG. 1 illustrates a simplified version of the oscillometric blood pressure monitor described in the aforementioned Ramsey patents. In FIG. 1, the arm 100 of a human subject is shown wearing a conventional flexible inflatable and deflatable cuff 101 for occluding the brachial artery when fully inflated. As the cuff 101 is deflated using deflate valve 102 having exhaust 103, the arterial occlusion is gradually relieved. The deflation of cuff 101 via deflate valve 102 is controlled by microprocessor 107 via control line 108.

A pressure transducer 104 is coupled by a duct 105 to the cuff 101 for sensing the pressure therein. In accordance with conventional oscillometric techniques, pressure oscillations in the artery are sensed by changes in the counter-pressure of the cuff 101, and these pressure oscillations are converted into an electrical signal and transducer 104 and coupled over path 106 to microprocessor 107 for processing. In addition, a source of pressurized air 109 is connected via a duct 110 through an inflate valve 111 and a duct 112 to the pressure cuff 101. The inflate valve 111 is electrically controlled through a connection 113 from the microprocessor 107. Also, the deflate valve 102 is connected by duct 114 via a branch connection 115 with the duct 112 leading to cuff 101.

Microprocessor 107 processes the signals from pressure transducer 104 to produce blood pressure data and to reject artifact data as described in the afore-mentioned Ramsey '029 and '034 patents. However, the blood pressure also can be determined in accordance with the teachings of Medero et al. in U.S. Pat. No. 4,543,962, of Medero in U.S. Pat. No. 4,546,775, of Hood, Jr. et al. in U.S. Pat. No. 4,461,266, of Ramsey, III et al. in U.S. Pat. No. 4,638,810, of Ramsey, III et al. in U.S. Pat. No. 4,754,761, of Ramsey, III et al. in U.S. Pat. No. 5,170,795, and of Ramsey, III et al. in U.S. Pat. No. 5,052,397, all of which are commonly assigned herewith and the disclosures of which are hereby incorporated by reference. Any of these known techniques are used to determine the quality of the oscillation complexes received at each level so that the blood pressure determination is made using actual blood pressure data and not artifacts.

During operation of the apparatus illustrated in FIG. 1, it is assumed that air under pressure to about 8–10 p.s.i. is available in the source of pressurized air 109. When it is desired to initiate a determination of blood pressure, the microprocessor 107 furnishes a signal over path 113 to open the inflate valve 111. The deflate valve 102 is closed. Air from the source 109 is communicated through inflate valve 111 and duct 112 to inflate the cuff 101 to a desired level, preferably above the estimated systolic pressure of the patient. Microprocessor 107 responds to a signal on path 106 from the pressure transducer 104, which is indicative of the instantaneous pressure in the cuff 101, to interrupt the inflation of the cuff 101 when the pressure in the cuff 101 reaches a predetermined value above the estimated systolic pressure of the patient. Such interruption is accomplished by sending a signal over path 113 instructing inflate valve 111 to close. Once inflate valve 111 has been closed, the blood pressure measurement can be obtained by commencing a deflate routine.

Actual measurement of the blood pressure under the control of the microprocessor 107 and the deflate valve 102 and as sensed by pressure transducer 104 can be accomplished in any suitable manner such as that disclosed in the aforementioned patents. At the completion of each measurement cycle, the deflate valve 102 can be re-opened long enough to relax the cuff pressure substantially completely via exhaust 103. Thereafter, the deflate valve 102 is closed for the start of a new measurement cycle.

Accordingly, when a blood pressure measurement is desired, the inflate valve 111 is opened while the cuff pressure is supervised by pressure transducer 104 until the cuff pressure reaches the desired level. The inflate valve 111 is then closed. Thereafter, the deflate valve 102 is operated using signal 108 from microprocessor 107 and the blood pressure measurement taken.

Prior art FIG. 2 illustrates a pressure versus time graph illustrating a conventional cuff step deflation and measurement cycle for a conventional NIBP monitor. As illustrated, the cuff 101 is inflated to a pressure above the systolic pressure, and the cuff 101 is then deflated in steps of equal duration of about 8 mm Hg per step. A timeout duration d is provided at each step during which the signal processing circuitry searches for oscillation complexes in accordance with the techniques described in the afore-mentioned commonly assigned patents. At the end of timeout duration d, the cuff pressure is decremented even if no oscillation complex is detected. This process of decrementing the pressure and searching for oscillation complexes is repeated at least until MAP and/or the oscillation envelope 200 may be determined. The entire blood pressure determination process is repeated at predetermined intervals which are typically set by the user.

During operation, pressure transducer 104 of FIG. 1 produces an output arterial pulse signal on path 106 which covers a large dynamic range. Accordingly, the measured signal is preamplified and then separated into high-resolution AC coupled and low-resolution DC coupled paths for processing. In particular, as shown in FIG. 3, the signal from a pressure transducer and amplifier 300 is input directly into an 8-bit A/D converter 302 and input into a pulse separation circuit 304 comprising, for example, a bandpass filter. The pulse separation circuit 304 is designed to reject the DC component of the arterial pulse pressure signal output by the pressure transducer and preamplifier 300 while amplifying the oscillation complexes. Typically, pulse separation hardware 304 passes those signals whose frequency components lie in a range from 1 to 10 Hz and strongly rejects other frequency components. The resulting oscillation complex signal is then input into an 8-bit A/D converter 306. As in the system of the Ramsey '034 and '029 patents, a single A/D converter may be used by placing a multiplexer between the A/D converter and the outputs of the respective paths.

As illustrated in FIG. 3, each sampled pressure point is represented by 8 binary bits which are routed to static pressure processing software 308 and oscillation complex signal processing software 310 prior to determination of the patient's blood pressure by blood pressure determination software 312. Typically, software 308–312 operates on microprocessor 107 of FIG. 1.

Thus, as described above with respect to FIGS. 1–3, NIBP measurement by the oscillometric method relies on measuring the amplitude of small "oscillations" in the cuff pressure at various static cuff pressures where the oscillations are a small fraction of the static cuff pressure (typically one percent). The electrical signal from the cuff pressure transducer is split into two channels: the static pressure signal "PT" which is directly DC coupled from the transducer and used to control and measure the static cuff pressure, and the oscillation complex signal "FPT" which is AC coupled to a high gain amplifier for providing an amplified representation of the oscillation complexes. As shown in FIG. 3, PT and FPT are separately digitized via two channels of an A/D converter (usually 8-bit or 12-bit converters) which has insufficient resolution to resolve the pulsatile component (oscillation complexes) in the presence of the static component. For this reason, separate processing channels have been necessary for measuring the pulse amplitude of the FPT signal while using the PT signal for cuff static pressure measurement and control. Unfortunately, such a two channel method complicates both the hardware and software of the blood pressure monitor.

It is, accordingly, a primary object of the present invention to digitize the pressure transducer signal with sufficient resolution to preserve the details of the pulsatile component so that the resulting "composite" arterial pulse signal can be processed directly to provide the oscillation complexes, thereby simplifying the resulting system.

It is a further object of the present invention to use a single processing channel to process the arterial pulse signals during a blood pressure determination.

It is also an object of the present invention to sum the arterial pulse signal from the pressure transducer with a dither signal at a frequency that forms an integral number of cycles in a summing interval for the samples so that the effective resolution may be enhanced without using an expensive high-resolution A/D converter.

SUMMARY OF THE INVENTION

The above objects have been met in accordance with the present invention by providing an automated sphygmomanometer which digitizes the pressure transducer output with sufficient resolution to preserve the details of the oscillation complexes. The "composite" arterial pulse signal containing the DC pressure component and the oscillation complexes can then be processed in a single processing channel so that the amplitudes of the oscillation pulse can be measured in the presence of the static components. Any necessary filtering is performed in the digital domain using known digital signal processing (DSP) techniques.

In addition, in order to minimize expense for the needed A/D converters, dither signals are added to the arterial pulse signal in the single processing channel in order to increase the apparent resolution. A simple finite impulse response (FIR) filter having zero crossings at the summing frequencies for the dither signal is then used to eliminate the dither signal prior to determining the blood pressure from the composite signal using pulse separation and blood pressure calculation software.

BRIEF DESCRIPTION OF THE DRAWINGS

The present invention will be better understood after reading the following detailed description of the presently preferred embodiments thereof with reference to the appended drawings, in which.

DETAILED DESCRIPTION OF THE PRESENTLY PREFERRED EMBODIMENT

A system and method which meets the above-mentioned objects and provides other beneficial features in accordance with the presently preferred exemplary embodiment of the invention will be described below with reference to FIGS. 4–6. Those skilled in the art will readily appreciate that the description given herein with respect to those figures is for explanatory purposes only and is not intended in any way to limit the scope of the invention. Also, common reference numbers are used throughout the drawings to represent common elements. All questions regarding the scope of the of the invention should be resolved by referring to the appended claims.

Figure 3:
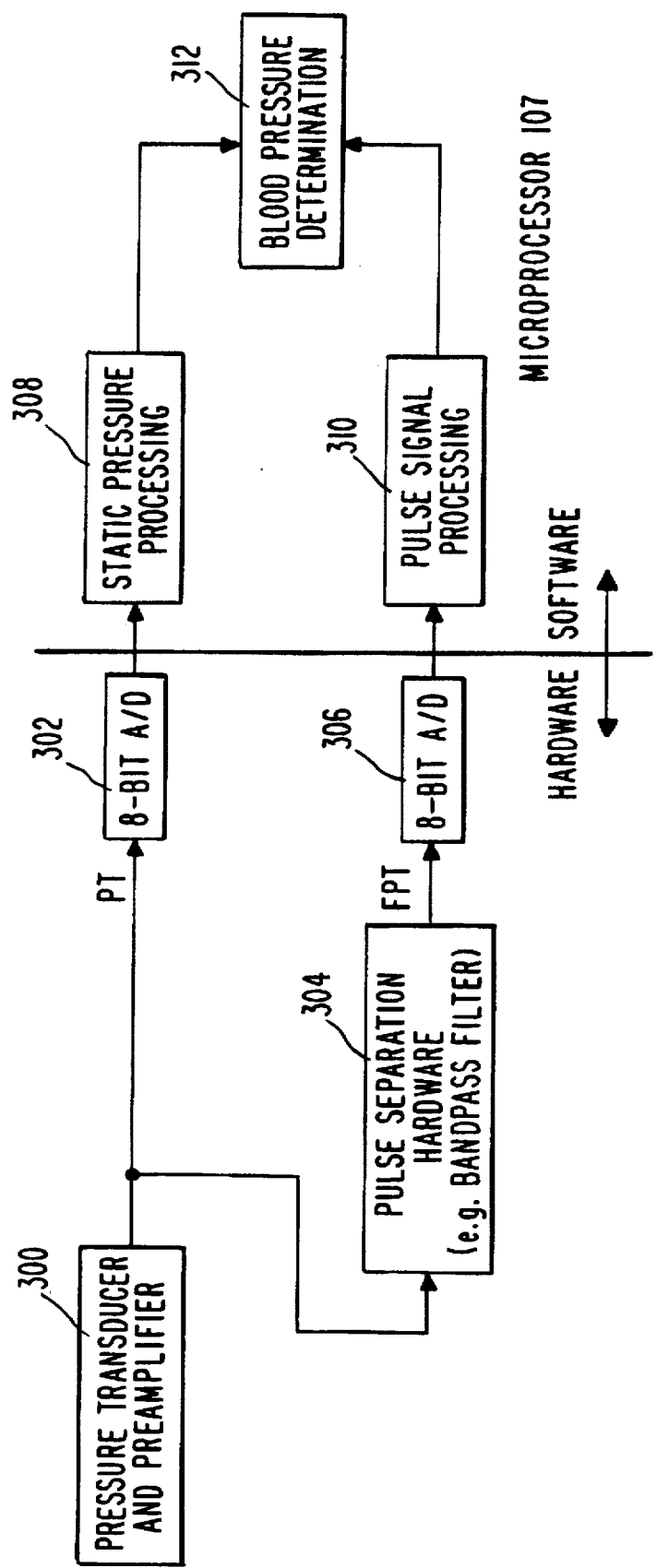
FIG. 3 is a simplified block diagram of the two-channel arterial pulse processing circuitry used in prior art oscillometric blood pressure monitors.
Figure 4:
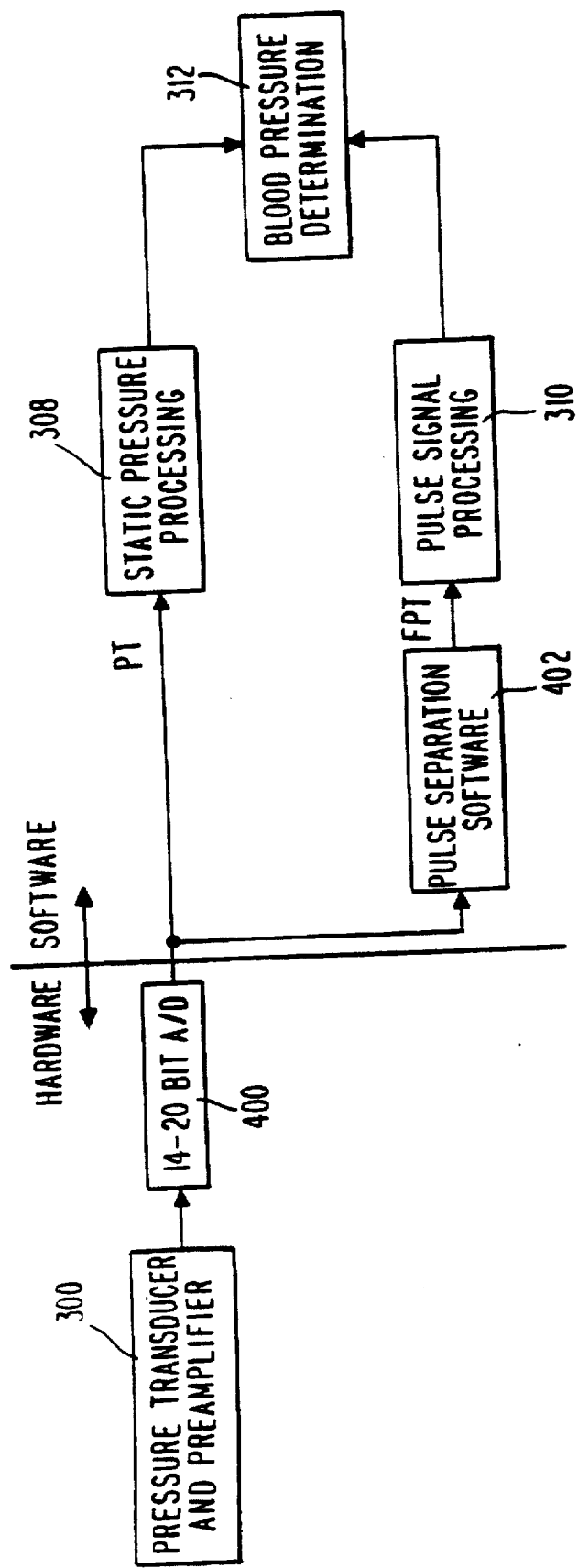
FIG. 4 is a simplified block diagram of a single channel arterial pulse processing circuit in accordance with the invention.

A single channel arterial pulse signal processing system in accordance with the invention is illustrated in FIG. 4. As shown, the output of the pressure transducer and preamplifier 300 is input into a single A/D converter 400 having, for example, 14–20 bit resolution. Such resolution allows the oscillation complexes to be resolved even in the presence of the static pressure components. The oscillation complexes and static pressure signals are then separated and processed by pulse separation software 402 using known DSP techniques. The remainder of the processing for determining the blood pressure is the same as in the prior art embodiment of FIG. 3.

The invention of FIG. 4 has been implemented using a 56ADC16 monolithic 16-bit A/D converter and a DSP56001 processor, both manufactured by Motorola. An A/D converter with at least 16-bits is presently preferred.

Unfortunately, it is relatively expensive to implement an embodiment with high-resolution A/D converters because of the high cost of high-resolution A/D converters. Moreover, such high-resolution A/D converters may be too large to fit into conventional NIBP monitors. It is thus desired to develop a composite channel system which still allows for the use of relatively low resolution A/D converters. Such a low resolution A/D converter will be described below with respect to FIGS. 5 and 6.

The present inventors have recognized that signals processed in NIBP monitors using the oscillometric technique typically require lower sampling frequencies than common A/D converters readily accommodate. The present inventors have also recognized that when several samples are summed at a fast rate that the accumulation of samples can be used as a high-resolution sample at a lower rate if the signal has visited many codes of the A/D converter during the summing interval. One way to force the signal to visit many codes of the A/D converter is to sum in an analog dither signal with an amplitude at the A/D converter of several sample units with a frequency that forms an integral number of cycles in the summing interval. A simple finite impulse response (FIR) filter created by the summing is then designed as a moving average lowpass filter having zero crossings at the summing frequencies so as to eliminate the dither signal. A simple "composite" signal circuit of this type is illustrated in FIG. 5.

Figure 1:
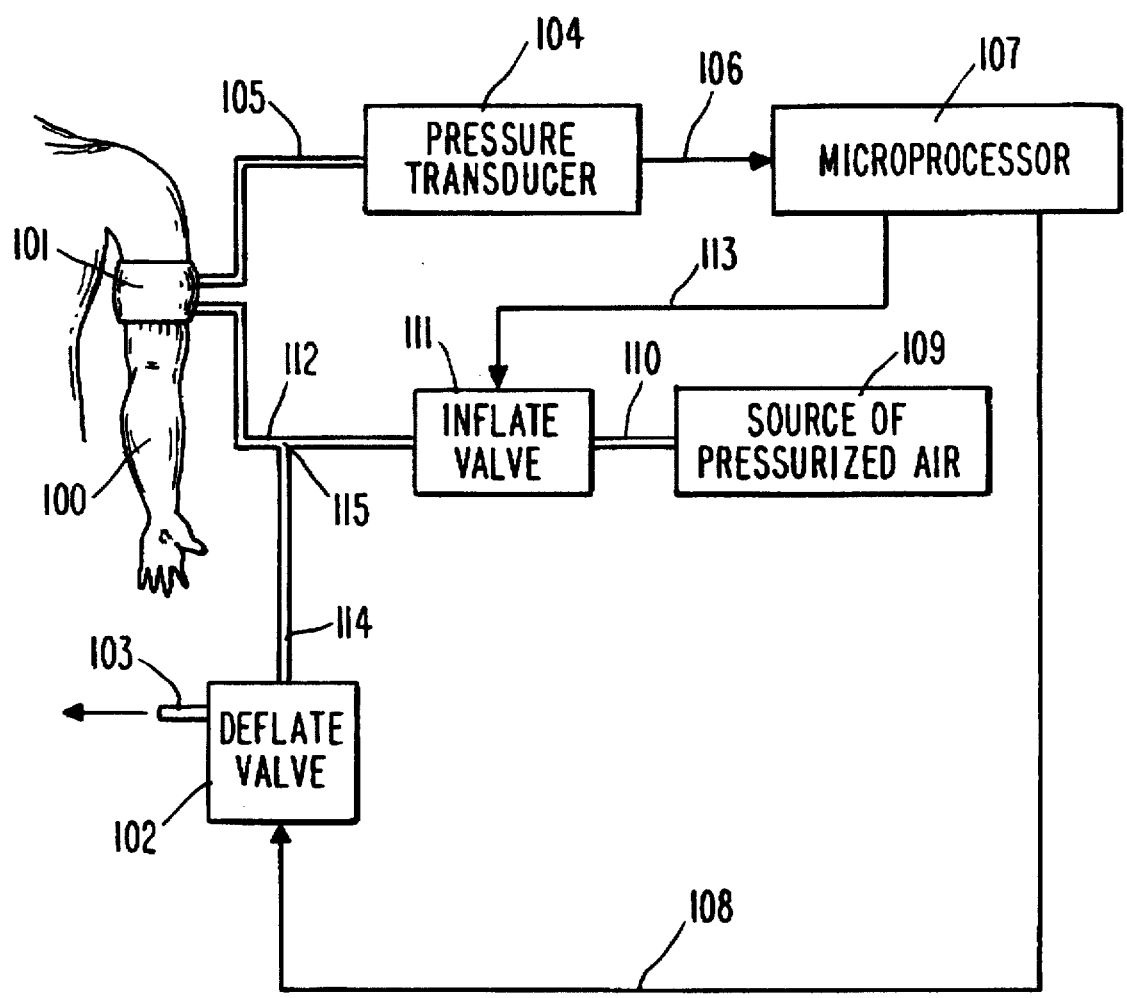
FIG. 1 is a schematic representation of a conventional noninvasive blood pressure ("NIBP") monitor of the type to which the present invention is directed.
Figure 2:
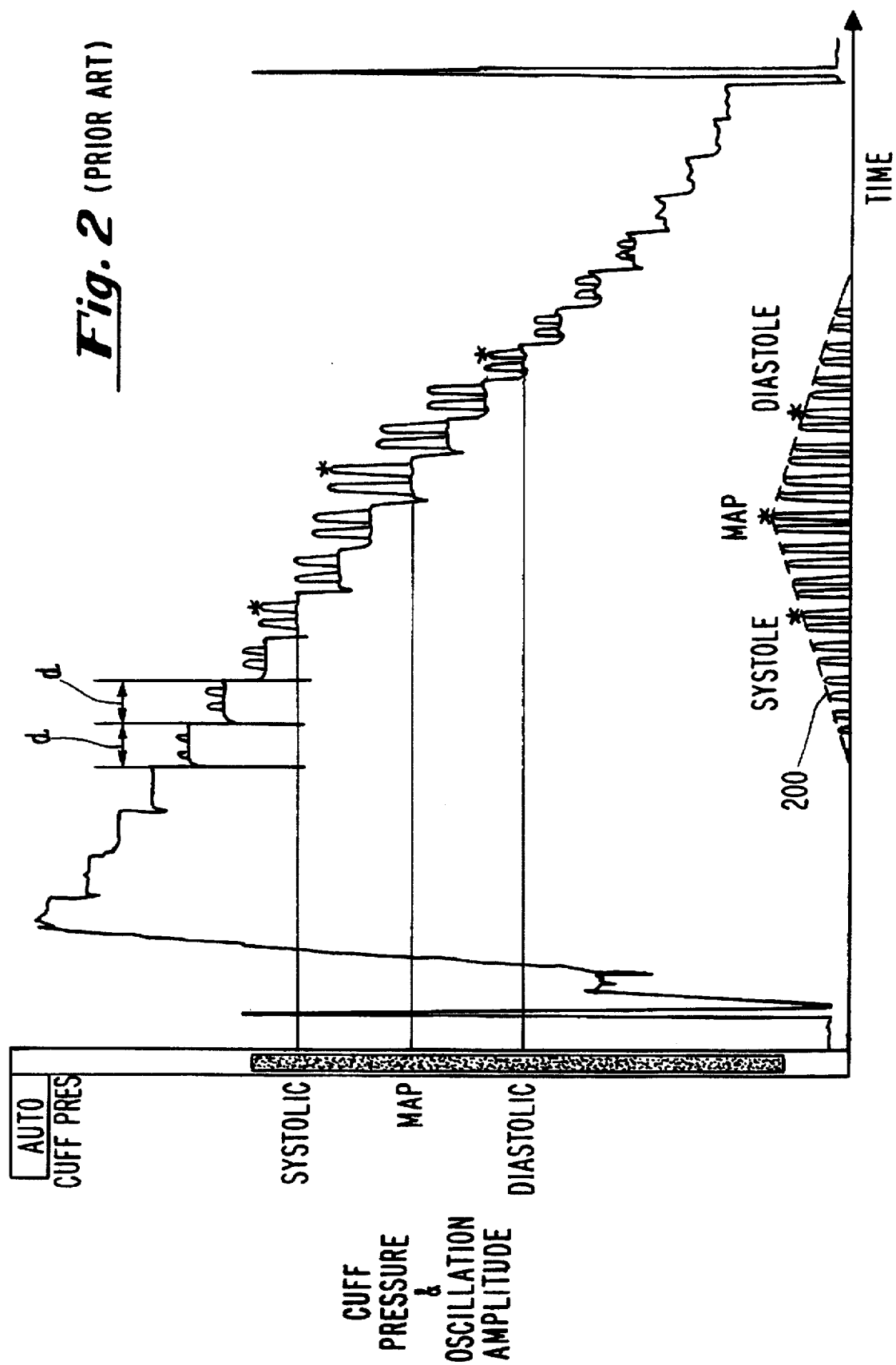
FIG. 2 is a pressure versus time graph illustrating a measuring cycle including step deflation steps and the corresponding oscillation complexes measured using a conventional NIBP monitor.
Figure 5:
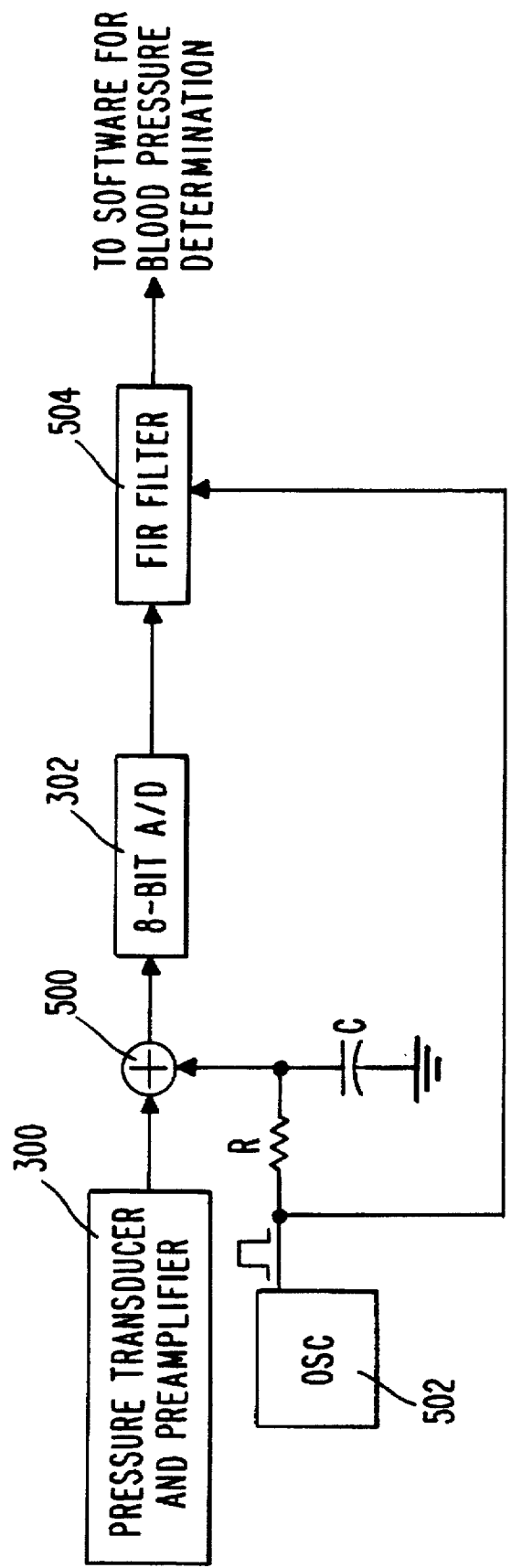
FIG. 5 is a simplified block diagram of a single channel arterial pulse processing circuit which implements dithering to increase the apparent resolution of the A/D conversion of the arterial pulse pressure signal.

As shown in FIG. 5, the output of pressure transducer and preamplifier 300 is input into an adder 500 which receives a dither signal from oscillator 502 via a RC coupling network. As noted above, the dither signal preferably has an amplitude corresponding to several units of the digitized output of the A/D converter 302. The sum signal from the adder 500 is then digitized by A/D converter 302 in the conventional manner. Of course, a higher resolution A/D converter 302 may also be used to produce still higher resolution without providing a higher resolution A/D converter. The output of A/D converter 302 is then input into an FIR filter 504 which removes the dither and sums the samples output from A/D converter 302. The output of oscillator 502 also can be used to set zero crossings in FIR filter 504 at the dither frequency so that the dither is eliminated from the sum signal. This is possible so long as the dither is provided a constant frequency and constant amplitude and is not random as in conventional dithering systems of the type described, for example, in U.S. Pat. Nos. 5,134,399 and 5,115,189. In a preferred embodiment, the dither signal from oscillator 502 is actually a square wave timing signal output by microprocessor 107 illustrated in FIG. 1.

Those skilled in the art will also appreciate that the embodiment of FIG. 5 is designed to improve the effective rate and resolution (number of bits) for A/D conversion of the composite signal. Those skilled in the art will also appreciate that by oversampling, for example, one hundred times, and then averaging the resulting dither signal over some predetermined time period, a FIR filter which zeros at the dither frequency will function as an effective low pass filter which removes the dither while providing a high resolution sum signal. Indeed, the present inventors have observed that the system of FIG. 5 may improve the effective resolution achieved from a 12-bit converter which sums 32 samples at 400 Hz to better than 16 bits. The summing characteristic of the FIR filter 504 may also serve as one section of a low pass filter for use in separating the PT signal from the FPT signal. Suitable FIR filters for this purpose are believed to be known to those skilled in the art.

As shown in FIG. 4, the output of the A/D converter 400 (or the circuit of FIG. 5) is input into software which separates the PT signal from the FPT signal and processes the resulting signals to determine the patient's blood pressure. Software for use with the dither circuit of FIG. 5 is illustrated in FIG. 6 and is preferably implemented by microprocessor 107.

Figure 6:
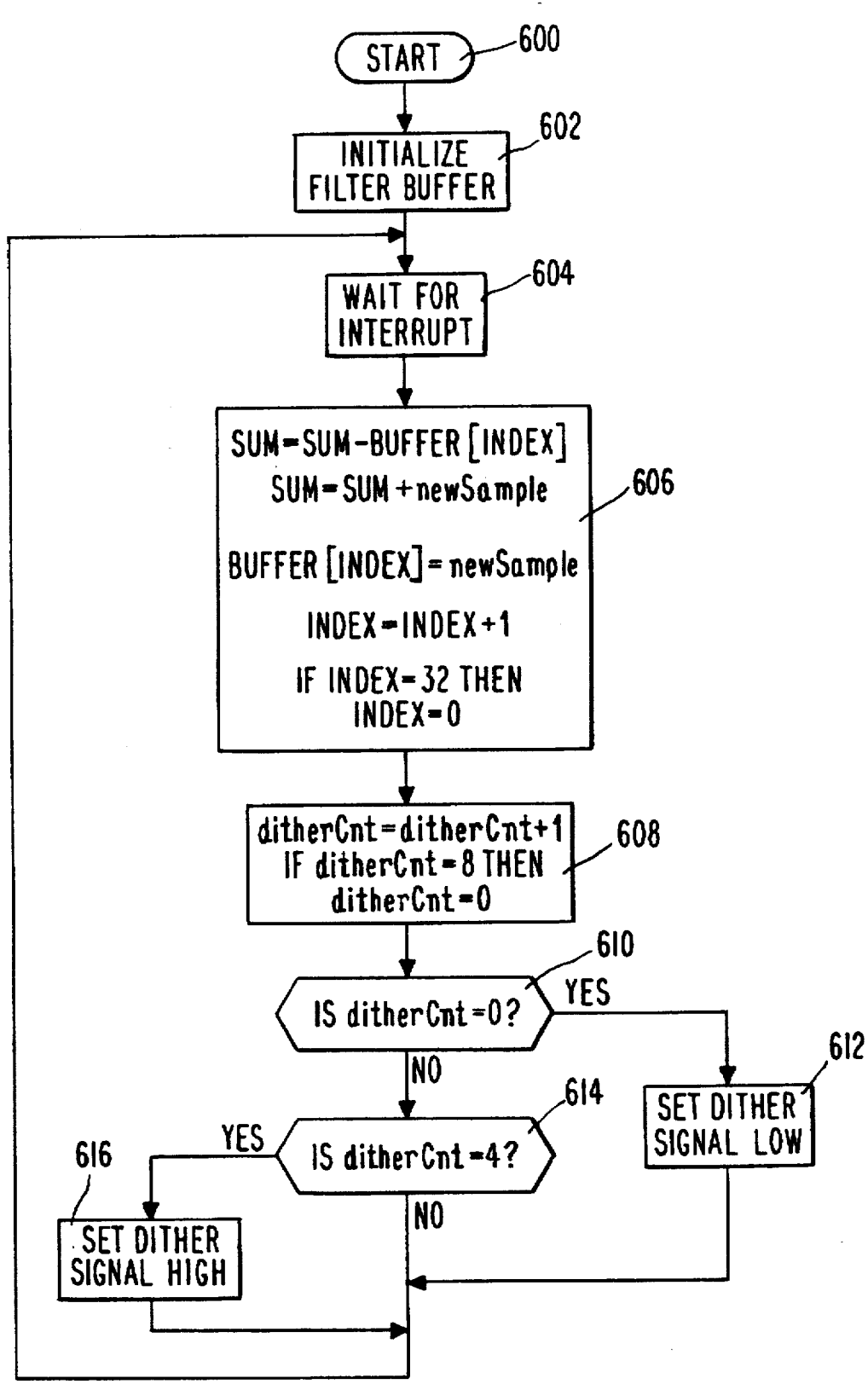
FIG. 6 is a flow diagram illustrating the dithering technique implemented in accordance with the invention.

As shown in FIG. 6, the dithering process starts at step 600 and initializes a filter buffer of the A/D converter 302 at step 602. Microprocessor 107 then waits for an interrupt at step 604 before updating the sample sum at step 606 to include the latest sample value.

In the illustrated embodiment, 8 successive samples are summed to produce a high resolution sum sample. Accordingly, at step 608 a dither counter is incremented to keep track of 8 loop iterations before the dither counter is reset to zero when the dither count reaches 8. At step 610, it is determined whether the dither count is equal to zero, and if so, the dither signal is set to a low value at step 612 before branching to step 604. However, if the dither count is not equal to zero, it is determined at step 614 whether the dither count is equal to 4, and if so, the dither signal is set to high value at step 616 before branching to step 604. Steps 608–616 thus cooperate to add a dither signal having a low value to the pressure transducer signal for dither counts 0–3 and a dither signal having a high value to the pressure transducer signal for dither counts 4–7. The resulting dither signal is then output by the oscillator 502, which as noted above, is preferably a timing output of the microprocessor 107. The dither signals are summed with the output of pressure transducer and preamplifier 300 at adder 500 prior to A/D conversion by A/D converter 302.

The present invention is advantageous in that it eliminates the requirement of an extra signal processing channel and the associated hardware. The present invention also substantially simplifies the signal processing algorithms. Moreover, improved resolution is provided at minimal cost.

It will be appreciated by those skilled in the art that the foregoing has set forth the presently preferred embodiment of the invention and an illustrative embodiment of the invention but that numerous alternative embodiments are possible without departing from the novel teachings of the invention. For example, those skilled in the art will appreciate that the techniques of the invention may be used for blood pressure monitors in which the pressure is incremented from diastolic pressure as described, for example, in U.S. Pat. No. 4,461,266 to Hood, Jr. et al. Also, those skilled in the art will appreciate that the techniques of the invention may be used for blood pressure monitors which do not use amplitude matching techniques described by Ramsey to determine whether oscillation complexes of sufficient quality have been received. In addition, those skilled in the art will appreciate that other dithering techniques may be used so long as the signal processing is not unduly complicated. Accordingly, all such modifications are intended to be included within the scope of of the appended claims.

We claim:

1. An automated sphygmomanometer apparatus, comprising:

an inflatable and deflatable pressure cuff;

inflating means operatively coupled to said cuff for selectively applying a medium under pressure to said cuff for inflating and pressurizing said cuff;

cuff pressure sensing means coupled to said cuff for sensing cuff pressure and outputting a composite cuff pressure signal including said cuff pressure and any blood pressure oscillations therein;

deflating means operatively coupled to said cuff for selectively relieving pressure from said cuff;

a dither signal source which provides a substantially constant amplitude dither signal at a substantially constant dither frequency;

means for summing said dither signal with said composite cuff pressure signal to produce a dithered composite cuff pressure signal;

an A/D converter which digitizes said dithered composite cuff pressure signal and provides an A/D converted output signal;

a finite impulse response filter which sums respective samples of said A/D converted output signal over a predetermined time period to form a high resolution sum signal and which has zero crossings at said dither frequency so as to eliminate said dither signal from said sum signal;

means responsive to said sum signal from said finite impulse response filter for digitally separating a first signal representing said cuff pressure from a second signal representing said blood pressure oscillations; and control means for controlling said inflating means to inflate said cuff and said deflating means to deflate said cuff during respective blood pressure determinations and for determining a blood pressure of a patient from said first and second signals.

2. An apparatus as in claim 1, wherein said dither frequency corresponds to an integral number of cycles of said predetermined time period.

3. A method of determining a patient's blood pressure using an automatic oscillometric blood pressure monitor comprising a pressurized cuff, means for inflating and deflating said cuff, means for measuring arterial pressure oscillation complexes through measurement of time varying pressures within said cuff, and means for determining a patient's blood pressure at predetermined measurement intervals by instructing said inflating and deflating means to inflate said cuff about an artery of the patient until said cuff is at a pressure level above the patient's estimated systolic pressure and to deflate said cuff by predetermined pressure decrements, by searching for arterial pressure oscillation complexes at each pressure level, and by determining, from said arterial pressure oscillation complexes, said patient's blood pressure, said method of determining a patient's blood pressure comprising the steps of:

inflating a pressure cuff about an appendage of a patient to a pressure above the patient's systolic pressure;

incrementally deflating said pressure cuff in predetermined pressure increments and outputting a composite cuff pressure signal at each pressure level, said composite cuff pressure signal including a cuff pressure signal and a blood pressure oscillation signal;

summing a substantially constant amplitude dither signal at a substantially constant dither frequency with said composite cuff pressure signal to create a dithered composite cuff pressure signal;

digitizing said dithered composite cuff pressure signal using an A/D converter and providing a digitized output signal;

summing respective samples of said digitized output signal over a predetermined time period to form a high resolution sum signal using a finite impulse response filter having zero crossings at said dither frequency so as to eliminate said dither signal from said sum signal;

digitally separating said cuff pressure signal in said sum signal from said blood pressure oscillation signal in said sum signal; and determining a blood pressure of said patient from said cuff pressure signal and said blood pressure oscillation signal.

4. An automated sphygmomanometer apparatus, comprising:

an inflatable and deflatable pressure cuff;

an inflate valve operatively coupled to said cuff which selectively applies a medium under pressure to said cuff for inflating and pressurizing said cuff;

a pressure transducer coupled to said cuff which senses cuff pressure and outputs a composite cuff pressure signal including said cuff pressure and any blood pressure oscillations therein;

a deflate valve operatively coupled to said cuff which selectively relieves pressure from said cuff;

a dither signal source which provides a substantially constant amplitude dither signal at a substantially constant dither frequency;

a summer which sums said dither signal with said composite cuff pressure signal to produce a dithered composite cuff pressure signal;

an A/D converter which digitizes said dithered composite cuff pressure signal and provides an A/D converted output signal;

a finite impulse response filter which sums respective samples of said A/D converted output signal over a predetermined time period to form a high resolution sum signal and which has zero crossings at said dither frequency so as to eliminate said dither signal from said sum signal; and a microprocessor which is programmed so as to digitally separate a first signal representing said cuff pressure in said sum signal from a second signal representing said blood pressure oscillations in said sum signal, programmed so as to control said inflate valve to inflate said cuff and said deflate valve to deflate said cuff during respective blood pressure determinations, and programmed so as to determine a blood pressure of a patient from said first and second signals.

* * * * *